(12) United States Patent
Pusiol

(10) Patent No.: US 7,659,124 B2
(45) Date of Patent: Feb. 9, 2010

(54) METHOD FOR THE DETECTION AND/OR ANALYSIS OF COMPOUNDS SIMULTANEOUSLY EXHIBITING NUCLEAR QUADRUPOLAR RESONANCE AND NUCLEAR MAGNETIC RESONANCE, OR DOUBLE NUCLEAR QUADRUPOLAR RESONANCE

(76) Inventor: Daniel J. Pusiol, Avda. del Tajamar No. 255, Alta Gracia, Cordoba (AR) 5186

( * ) Notice: Subject to any disclaimer, the term of this patent is extended or adjusted under 35 U.S.C. 154(b) by 876 days.

(21) Appl. No.: 10/713,344

(22) Filed: Nov. 14, 2003

(65) Prior Publication Data
US 2005/0202570 A1   Sep. 15, 2005

(30) Foreign Application Priority Data
Jun. 11, 2003   (AR) .............................. P030102080

(51) Int. Cl.
*G01N 24/00* (2006.01)
(52) U.S. Cl. .................. 436/173; 324/307; 324/309
(58) Field of Classification Search .................. None
See application file for complete search history.

(56) References Cited

U.S. PATENT DOCUMENTS

| | | | |
|---|---|---|---|
| 4,887,034 A | 12/1989 | Smith et al. |
| 5,206,592 A | 4/1993 | Buess et al. |
| 5,229,722 A | 7/1993 | Rommel et al. |
| 5,233,300 A | 8/1993 | Buess et al. |
| 5,457,385 A | 10/1995 | Sydney et al. |
| 5,491,414 A | 2/1996 | Smith et al. |
| 5,583,437 A | 12/1996 | Smith et al. |
| 5,592,083 A | 1/1997 | Magnuson et al. |
| 5,608,321 A | 3/1997 | Garroway et al. |
| 5,804,967 A | 9/1998 | Miller et al. |
| 6,054,856 A | 4/2000 | Garroway et al. |
| 6,100,694 A | 8/2000 | Wong |
| 6,104,190 A | 8/2000 | Buess et al. |
| 6,127,824 A | 10/2000 | Smith et al. |
| 6,166,541 A | 12/2000 | Smith et al. |
| 6,194,898 B1 | 2/2001 | Magnuson et al. |
| 6,522,135 B2 | 2/2003 | Miller et al. |

FOREIGN PATENT DOCUMENTS

| | | |
|---|---|---|
| RU | 2184368 C1 | 6/2002 |
| RU | 2190842 C1 | 10/2002 |
| WO | WO9809178 | 3/1998 |

OTHER PUBLICATIONS

Osán et al. "NQR: From imaging to explosives and drugs detection", Physica B, 2007, v. 389, pp. 45-50.*

(Continued)

*Primary Examiner*—Yelena G Gakh
(74) *Attorney, Agent, or Firm*—Volpe and Koenig, P.C.

(57) ABSTRACT

The present invention contributes to the resolution of the problem of detecting, for example, plastic explosives, which are not easily detected by conventional inspection techniques, as those based on X-ray apparatuses; or those using more sophisticated means from traces of explosive material which may remain, "contaminating" the external surface of luggage. As regards the first technique, the invention has an additional advantage in that it is fully automatic, that is, it is independent from the operator's ability to interpret low contrast images. As regards the second technology, the main advantage of the present invention consists of its speed and safety when inspecting luggage.

7 Claims, 8 Drawing Sheets

OTHER PUBLICATIONS

Kim et al. "Experimental Investigations of the Strong Off-Resonant Comb (SORC) Pulse Sequence in 14N NQR", Z. Naturf., 1992, v. 47a, pp. 415-420.*

Cerioni et al. "A New Method to Obtain Frequency Offsets in NQR Multi-Pulse Sequences", Hyperfine Interactions (2004) 159:389-393.*

J. Perlo, "Imágenes Codificadas Espacialmente Por *RMN* Y Detectadas Por *RCN*", Final Paper for the Physics Degree, College of Mathematics, Astronomy and Physics, Universidad Nacional de Códoba, Argentina (2000).

C. R. Rodriguez, "Estudio De La Dinamica Lenta Y La Estructura En Cristales Liquidos Liotropicos Micelares, Mediante RMN", Doctorate Thesis, College of Mathematics, Astronomy and Physics, Universidad Nacional de Códoba, Argentina (2000).

E. Rommel, K. Mischker, G. Osswald, K.H. Schweikert and F. Noack, A Powerful NMR Field-Cycling Device Using GTOs and MOSFETs for Relaxation Dispersion and Zero-Field Studies, J. Magn. Reson. 70, 219-234 (1986).

D. Tomasi, E.C. Caparelli, H. Panepucci and B. Foerster, "Fast Optimization of a Biplanar Gradient Coil Set", J. Magn. Reson. 140, 325-339 (1999).

E.C. Caparelli, D. Tomasi and H. Panepucci, "Shielded Biplanar Gradient Coil Design", J. Magn. Reson. 9, 725-731 (1999).

Y.K. Lee, H. Robert and D.K. Lathrop, "Circular Polarization Excitation and Detection in $^{14}$N NQR", J. Magn. Reson. 148, 355-362 (2001).

A.F. Privalov, S.V. Dvinskikh and H.-M. Vieth, "Coil Design for Large-Volume High-$B_1$ Homogeneity for Solid-State NMR Applications", J. Magn. Reson. A 123, 157-160 (1996).

V.S. Grechishkin, "NQR Device for Detecting Plastic Explosives, Mines and Drugs", Applied Physics, vol. A55, pp. 505-507 (1992).

B. Herzog and E.L. Hahn, "Transient Nuclear Induction and Double Nuclear-Resonance in Solids", Phys. Rev. vol. 103, No. 1, pp. 148-166 (1956).

J. Perlo, F. Casanova, H. Robert and D.J. Pusiol, "Solid State Proton Imaging Detected by Quadrupole Resonance", J. Magn. Reson. 150, 132-136 (2001).

E. Rommel, P. Nickel, R. Kimmich, and D. Pusiol, "Rotating-Frame NQR Imaging", J. Magn. Reson. 91, 630-636 (1991).

V.S. Grechishkin, "Application of Multipulse Sequences in Remote NQR", Appl. Phys. A58, pp. 63-65 (1994).

G.V. Mozjoukhine, "The Frequency Offset Effects of NQR of Spin $I=1$ for Remote Detection", Z. Naturforsch. 57 a, pp. 297-303 (2002).

* cited by examiner

METHOD FOR THE DETECTION AND/OR ANALYSIS OF COMPOUNDS SIMULTANEOUSLY EXHIBITING NUCLEAR QUADRUPOLAR RESONANCE AND NUCLEAR MAGNETIC RESONANCE, OR DOUBLE NUCLEAR QUADRUPOLAR RESONANCE

FIELD OF INVENTION

This invention refers to a method, sensor elements and arrangement for the detection and/or analysis of compounds simultaneously exhibiting nuclear quadrupolar resonance and nuclear magnetic resonance, or double nuclear quadrupolar resonance. More specifically, said method is related to the detection and/or analysis of compounds, particularly explosives, drugs, etc., placed in various kinds of containers, particularly luggage, mail, etc.

BACKGROUND

Nuclear quadrupolar resonance (NQR) is the response of a certain compound containing any quadrupolar nucleus to a high frequency pulse which is applied "on resonance". It is specifically used for the detection of explosives and other forbidden substances which may be hidden within luggage and packages, which substances detection is currently difficult. The apparatus has two versions: one of them to be used for hand luggage, i.e. briefcases, bags, purses, etc., the other version to be used in bigger luggage pieces such as those usually transported in aircrafts holds.

Quadrupolar resonance technique is absolutely harmless to environment, luggage and humans, as it involves luggage radiation with radio waves of very long wavelength or of low frequency -on the order of some MHz-, along with the simultaneous application of magnetic field pulses amounting to some tens of Gauss, even fewer than those applied in the known magnetic resonance imaging (MRI). This technique application is direct, and previous conditioning of objects to be inspected is not required. This method implies very quick routine inspections. Typically the verification for explosives in luggage or transported packages takes one or two seconds without neither opening same nor contacting them with any mechanical and/or palpation tool. No ionizing radiations are used, thus avoiding any danger to luggage or individuals. Detection is univocal and each apparatus is fully computerized, this fact allowing an easy operation which dispenses specialized personnel who should have to make subjective decisions.

Nuclear quadrupolar resonance (NQR) is an spectroscopic technique of frequent use in chemical and physical analyses of non-metal materials. Response generated by the nuclear quadrupolar resonance (NQR) is characteristic of magnetic and electric properties of resonant nuclei. The nuclear quadrupolar resonance (NQR) phenomenon may only take place with certain atoms (which nuclei exhibit nonnull quadrupolar moment, namely spin $I > \frac{1}{2}$), and is frequently easily observed when same are part of crystalline or amorphous materials. Thus, for example, all those explosives containing chlorine and/or nitrogen are potentially detectable by means of this technique.

Nitrogen nuclear quadrupolar resonance (NQR) signals in RDX and other explosives (e.g., see: V. S. Grechishkin, "NQR device for detecting plastic explosives Mines and Drugs", Applied Physics, Vol. A55, pp. 505-507 (1992)) have already been observed with sensitivity enough to form the base of a detector capable to be used in order to investigate traveling bags and closed mail, personal carriers, etc. The resonance phenomenon in nitrogen substances is mainly observed in the high frequencies range, i.e. explosive detection is accomplished through radio waves, conveniently conditioned by means of special electronic devices. Each chemical compound the explosive substance is composed of may possess one or more resonance frequencies which are generally unique and help to distinguish same from other compounds present in nature.

Electric and magnetic properties of atomic nuclei produce the nuclear quadrupolar resonance (NQR) phenomenon. Nuclei with spherically non-symmetrical electric charge possess a quadrupolar electric moment. Other nuclear property consists of the possession of a magnetic moment, also known as nuclear spin. Nuclear quadrupolar resonance originates upon the interaction between the nucleus electric quadrupolar moment and the [gradient of] electric field originated from the electric charges adjoining the nucleus.

Graphically, albeit not in a rigorous manner: it can be said that when a quadrupolar nucleus experiments an electric field gradient resulting from an atomic environment, this occurs as if different portions of the nucleus were experiencing a torque making them to precess (rotate) around the maximum variation axis direction (gradient) of the electric field in the quadrupolar nucleus position. This precession movement "drags" the nuclear magnetic moment. Should the sample be temporarily subjected to an oscillating magnetic field, "tuned" with this precession, the nuclear magnetic moment orientation as regards the electric field gradient direction could be modified. Such oscillating electric field is simply achieved by placing the sample or object to be detected at the vicinity of an antenna which is connected to a radio frequency generator during a convenient period of time (typically on the order of microseconds) known as "radio frequency pulse". Upon the termination of the pulse, the magnetization of the sample, which precesses with the quadrupolar resonance frequency, produces a detectable signal known as "free induction decay signal", usually named "FID".

The above mentioned precession frequency depends on two parameters:
firstly it is proportional to the quadrupolar moment P of the nucleus, which is in turn related to the internal electric charge distribution of said quadrupolar nucleus. P parameter is zero in those cases in which the charge distribution of the nucleus has a spherical symmetry, positive when the charge distribution is elongated along the main axis, and negative when it is flat relative to said axis. Symmetry properties of the nucleus require that a necessary condition for the nucleus P to be different from zero is that the spin quantic number (or magnetic quantic number) be higher than one half: $I > \frac{1}{2}$; and
secondly, frequency is controlled by the electric field's main component, q.

For example, in the case of a group of spin $I=\frac{3}{2}$ nuclei, resonance frequency when no external magnetic field is present is given by: $v = e^2qP/4h$, h being the Planck's constant and e the electron charge. In the case of nuclei with spin $I=1$, up to three resonance frequencies can be observed, namely: $v_{+/-} = (3e^2qP/4h)$ $(1+/-\eta/3) y v_o = (e^2qP/2h)\eta$, wherein $\eta$ is termed electric field gradient asymmetry parameter.

The purpose of these definitions is to show that the resonance frequency value, which may be measured with high accuracy in any nuclear quadrupolar resonance (NQR) experiment, is a characteristic magnitude of the molecule bearing the resonant nucleus, such as a "fingerprint". There exist in nature many different quadrupolar nuclei. Those commonly present in explosives are nitrogen, chlorine, sodium, potassium, etc. All of these nuclei are detected by routine in nuclear quadrupolar resonance (NQR) spectrometers used in scientific research, and the same happens in the case of explosives. For example, it is possible to inspect the presence of different explosives by adjusting the detector to the characteristic frequence(s) of said molecule, which must be previously well known.

Many devices which use pure quadrupolar resonance have been invented in order to detect different forbidden compounds or substances. As used herein, "pure" means the non-inclusion of an external magnetic field, also known as "Zeeman magnetic field".

Generally, compounds are crystalline solids characterized in that the free induction decay signal (FID) and the shape of the nuclear resonance line of a group of spins A nuclei are mainly defined by the coupling of their magnetic moments to the magnetic moments of another group of different spins B nuclei. In these cases coupling within the same spins A may be neglected, and consequently the loss of coherence regarding the precession phase of spins A is due to fluctuations in local magnetic fields generated by spins B, which occupy neighboring positions in the crystalline net or in the molecule itself. A previous work by Herzog and Hahn (B. Herzog and E. L. Hahn, Phys. Rev. 103, 148 (1956)), demonstrates that by applying a weak magnetic field $H_0$ (on the order of some Gauss) and by continually irradiating protons in resonance condition with an oscillating $H_2$ magnetic field, said coupling can be destroyed. As the decaying time of cross coherence of quadrupolar nuclei is almost exclusively due to fluctuations of local fields produced by the protons, protons double radiation averages said fields to zero, producing a remarkable increase of the decay time of magnetization of the group of spins A nuclei.

Physical explanation is that the line width of spins A suffers a marked narrowing when the externally forced reorientation speed of spins B is sufficiently high so as to cause the reduction to small values of the mean value of the local field produced in the spins A nuclei group. This average is similar to the effect known as "motional narrowing" in liquids, to the "line narrowing" obtained upon the mechanical rotation of liquid samples in a non-uniform external magnetic field, and also to the "spinning" or mechanical rotation of solids, to narrow the nuclear magnetic resonance (NMR), broadened by local magnetic fields. In order for the mechanical rotation to be effective, rotation speed must exceed the broadening of Larmor frequencies produced by the lack of field homogeneity. Similarly, line narrowing due to the double resonance in solids requires that the speed of reorientation of spins B to exceed the minimum broadening in Larmor frequencies of spins A, existing upon the lack of double resonance. With the experiment of double resonance, decay time of the envelope of the spin echoes of spins A, known as $T_2$, increases or decreases depending on a combination of effects:

1) internal couplings among spins A (homonuclear coupling); and
2) coupling between spins A and B (heteronuclear coupling).

For an oscillating magnetic field $H_2$ with adequate intensity, which also accomplishes the resonance condition for spins B in weak magnetic field $H_0$, the decay time as regards the envelope of echoes $T_2$ is extended up to the theoretical maximum limit imposed by the time extension of longitudinal decay $T_1$, or otherwise by the time extension of decay $T_2$ of spins A, whichever the lower.

SUMMARY

The present invention contributes to the resolution of the problem of detecting, for example, plastic explosives, which are not easily detected by conventional inspection techniques, as those based on X-ray apparatuses; or those using more sophisticated means from traces of explosive material which may remain, "contaminating" the external surface of luggage. As regards the first technique, the invention has an additional advantage in that it is fully automatic, that is, it is independent from the operator's ability to interpret low contrast images. As regards the second technology, the main advantage of the present invention consists of its speed and safety when inspecting luggage.

Preferably, the invention refers to the detection of compounds which may be located both outside the detector volume, as in the case of a "superficial" type detecting device, and inside the volume thereof, as in the case of the so-called "volumetric detectors". Neither case requires the invasion of the internal volume of inspected luggage or object. Accordingly, as regards both detector types -volumetric and superficial- we consider the proposed method as a "remote detection" one. Although this definition is not completely exhaustive, the remote detection method refers to the situation in which the object or compound to be detected is located outside the physical plane occupied by the excitation/detection device of the detector, frequently at a distance which may be compared to the dimensions of the detector. As regards superficial detectors, the method of detection may be termed as "one side detection method", that is, it detects the compound or object searched for from one side of the luggage containing same. Although the use of this device necessarily implies a sensitivity reduction, and thus the minimum volume of detectable compound, said device allows an easier identification of the position of the compound within the volume of the containing luggage. In the case of volumetric detectors, as already stated, they posses a lower minimum detection threshold for the compound to be detected. Nevertheless, both designs are complementary, it being possible to use a volumetric detector during the first step or routine detection, and then identify the exact position of the explosive by means of a superficial detector. From now on we will refer to volumetric detectors, it being possible to extend the utilization thereof merely by changing the design of the detection device by the design of a superficial one.

Double resonance, or DOR, is applied as follows: as the quadrupolar resonance of spins A is directly observed through, for example, spin echoes, spins B are simultaneously irradiated with continuous waves or pulses, at their magnetic resonance frequency, which necessarily differs from that of spins A and is determined by $\gamma H_0$, $\gamma$ being the nuclei gyromagnetic coupling factor. Local field fluctuations are averaged due to a forced reorientation of spins B, affecting the cross coherence decay time of spins A. In such a situation, spins A signal constitutes an indicator of the resonance of B. When the coupling between spins A and B is strong enough, the DOR is easily detected. This kind of resonance was proposed in the literature in order to study this type of coupling (B. Herzog and E. L. Hahn, Phys. Rev. 103, 148 (1956)). The double resonance method also allows the finding of resonance frequencies of the spins B nuclei group, which could be remarkably low; measurement of their lines shape is also possible.

Amplitude of spin echo of A nuclei (nuclear quadrupolar resonance of $^{14}$N or $^{35}$Cl or $^{37}$Cl) increases exponentially as time between pulses τ of π/2 and π decreases; the signal-to-noise ratio, and thus the detector sensitivity, being the parameter to be improved. Time τ can be decreased in a limited way, as in practice, once the radio-frequency pulse ends, there appears a dead time (actually known as spectrometer dead time) which masks the echo signal. Upon the increase of the spin-spin decay time $T_2$ of spins A, due to spins B resonance, the result is that for the lowest possible τ (or for that allowed by spectrometer electronics) a considerable increase of spin echo is produced, precisely from the spins A nuclei group.

The DOR method has been used in order to code the spatial density of nuclei, thus being transformed in a method for solids imaging, known as DRI, as described by J. Perlo et al. (J. Perlo, F. Casanova, H. Robert and D. J. Pusiol, "Solid state proton imaging detected by quadrupole resonance", J. Magn. Reson., 150, I (2001). This work details the method used for the obtention of optimum conditions between the value of a weak static magnetic field $H_0$ and a low frequency magnetic field $H_2$, and the application to a particular compound.

It is known that a weak magnetic field $H_0$, when applied to polycrystalline compounds during the period of the quadrupolar signal detection, strongly broadens the resonance line and, at the same time, the information contained by the spectrum is lost. This phenomenon is fully discussed by E. Rommel, P. Nickel, R. Kimmich and D. Pusiol in "NQR Imaging", J. Magn. Reson. 91, 630 (1990) and by the references therein. That is to say, in practice we see a double effect: firstly, inclusion of the double resonance induces a strong decrease of the cross magnetization decay, with a significant improvement as regards the signal-to-noise ratio of the signal; and secondly, in those cases where spins B should be uncoupled from the quadrupolar nucleus in order to be observed by nuclear magnetic resonance (NMR) (as in the case of protons), the line broadens producing a loss in the same signal-to-noise ratio.

It is to be noted that, as stated by Herzog and Hahn's original work, spins B resonance is not limited to the nuclear magnetic resonance of protons but it can be extended to the nuclear magnetic resonance (NMR) of fluorine, phosphorous, etc.; or to the quadrupolar resonance of nuclei groups possessing a small quadrupolar coupling constant. In the later case we will see that the DOR would occur among groups of quadrupolar nuclei, being unnecessary the application of the weak static magnetic field $H_0$. This subject shall be further discussed hereinbelow.

This invention proposes the application of magnetic field $H_0$ by means of pulses. Basic and main idea is to attain two simultaneous effects:

1) to improve the signal-to-noise ratio by applying DOR, and
2) to allow the digitalization of the quadrupolar sign of spins A in the pure nuclear quadrupolar resonance condition or, in other words, without the application of any external magnetic field.

That is to say, we turn on the $H_0$ magnetic field (which along with the low frequency field $H_2$ generates the magnetic resonance on spins B), in coincidence with the first high frequency pulse of π/2 of field $H_1$, the later being applied in quadrupolar resonance condition on spins A preferably in a spin-echo sequence (i.e. we attain the DOR condition), and we turn it off just when the detected quadrupolar resonance signal echo of the spins A themselves achieves its maximum intensity, which is when the digitalization and summing of detected signals begins. During such process the low frequency field $H_2$ must remain on. This sequence we will call PUDOR, from PUlsed DOuble Resonance. Upon the completion of the digitalization and summing of said detected signals, the $H_0$ on/off sequence is repeated until an adequate signal-to-noise ratio for the detection and/or analysis of the compound is obtained. Once said adequate signal-to-noise ratio is obtained, an alarm signal will be emitted upon a positive detection, or upon a negative detection the detection and/or analysis of the following compound will take place.

Should an adequate signal-to-noise ratio not be obtained before the effective relaxation of the quadrupolar signal of spins A, an additional sequence of detection and/or analysis will take place, consisting of the storage of the obtained signals; waiting for the relaxation of said group of spins A until they thermally balance with the network, the commencement of a new on/off sequence of $H_0$, and calculation of the average between the new obtained signals and those previously stored. This additional sequence shall be carried out as many times as is necessary until the obtention of an signal-to-noise ratio which is adequate for the detection and/or analysis of the compound.

Upon the obtention of said signal-to-noise ratio, said alarm signal will be emitted, should a positive detection occur, or the next compound or object will be detected and/or analyzed should the result be negative.

It must be remarked that the definition of high and low frequency of excitation associated to the $H_1$ and $H_2$ magnetic fields which application is defined on the nuclei group of spins A (nuclear quadrupolar resonance) and the nuclei group of spins B (nuclear magnetic resonance) respectively, means that field $H_1$ oscillates in a frequency higher than that of field $H_2$. Generally, field $H_1$ is on the order of the Mhz, while field $H_2$ is on the order of some tens or hundreds of Khz. Nevertheless, below we will explain the particular situation of some compounds which quadrupolar resonance characteristic requires that field $H_1$ oscillate in a frequency on the order of a few Mhz. Further, the allocation of spins A and B nuclei groups is done in such a manner that said group of spins A is that group exhibiting the best pure nuclear quadrupolar resonance (NQR) signal.

This procedure is not limited to the combination of PUDOR with the spin-echo sequence, but extends to all of the known pulse sequences, both those consisting of single pulses and composite pulses. More precisely, we will group said pulse sequences as "steady" and "non-steady" sequences. The steady group includes, for example:

i) the sequence from steady state free precession or SSFP which consists of radiating the sample with successive pulses of π/2 on spins A and digitalize the quadrupolar signal originating therefrom during intervals between pulses. In this case, field pulse $H_0$ begins, coinciding with each pulse of π/2 of field $H_1$ and ends at a convenient time selected between successive pulses of π/2; and ii) sequence known as Strong Off Resonant Comb or SORC pulses (e.g. see V. S. Grechishkin, Appl. Phys. A58, 63-65 (1994), or G. V. Mozjuokhine, "The frequency offset effects of NQR of spin I=1 for remote detection", Z. Naturforschung, vo. 57a, pp. 297-303 (2002)), a variant of the SSFP, wherein the quadrupolar signal is excited and detected in the off-resonant condition. This sequence applies composite pulses of different amplitude and phases, which amplitudes α and β are equally spaced in time. Again, the detection signal is built by means of the digital sum of several hundreds or thousands of nuclear quadrupolar resonance (NQR) signals which follow each composite pulse of the SORC sequence, simultaneously combining the double radiation and pulses of magnetic field $H_0$ at the semi-period comprising excitation pulses of the high frequency magnetic field $H_1$, and part of the free evolution period between high frequency pulses, during the time the radiation remains on, with a low frequency magnetic field $H_2$.

"Non-steady" sequences group comprises those which maintain the signal of the nuclear quadrupolar resonance (NQR) echo during a time (called "effective $T_2$") longer than the decay $T_2$ of Carr and Purcell pulses sequence. These are those called "Spin Lock Spin Echo" or SLSE, and that of Carr, Purcell, Meiboom and Gill or CPMG. A practical description thereof may be found in R. Kimmich, "NMR-Tomography, Diffusometry Relaxometry", Springer (1997). The SLSE technique consists of the application -to the compound to be detected- of a high frequency pulse of amplitude such to be able to reorient quadrupolar nuclei magnetization at a 90° angle and with a 0° phase for the synthesized signal generator. After a period of time τ, a second high frequence pulse is applied which lasts twice or reorientates sample in 180° and in a 90° phase with respect to the first pulse. The spin echo appears exactly at a same period of time T, since the end of the high frequency second pulse. Later another 180° pulse with a 90° phase is applied, the second echo amplitude being smaller than the first, then a third high frequency pulse is applied and the third echo appears -which amplitude is always slightly lower than the precedent one- and so on until n echoes are collected (typically hundreds and thousands thereof). The so-called "detection signal" is the amplitudes collection of all of the echoes, digitalized and summed together. In many practical cases it is possible to replace both the first and the second high frequency pulse by the so-called "composite pulses" (see Agreev et al., "Composite pulses in nuclear quadrupole resonance", Molecular Physics, vol. 83, pp. 193-220 (1994)) with the purpose of considerably increasing the detection efficiency.

In this invention particularly, we disclose a variant of the three above mentioned sequences for steady and non-steady pulses, which may be applied both to the double resonance DOR condition and pulsed double resonance PUDOR, which is obtained from the application of a process of resonant excitation and off resonant detection, which we will call TONROF (Transmission ON resonance-Reception OFF resonance") to said both steady and non-steady sequences, which will be described below.

Basic idea of these pulse sequences is to obtain the highest possible number of signals to average, without having to wait the necessary time for the spins A nuclei group to relax again up to the thermal balance with the network, before the experiment is repeated. The necessary period of time to reach said thermal balance is typically of at least 5 times the longitudinal relaxation time $T_1$ of spins A. In every case it is possible to replace pulses of π and π/2 by multiple pulse trains which purpose is to improve sensitivity and conditions within which resonance is achieved. To such effect, we can mention G. V. Mozjoukhine, Z. Naturforschung, 57 a, 297-303 (2002).

Thus, it is an object of the present invention a method for the detection and/or analysis of compounds which simultaneously exhibit nuclear quadrupolar resonance and nuclear magnetic resonance, said compounds comprising a spins A nuclei group capable of exhibiting a quadrupolar resonance; and a spins B nuclei group, capable of exhibiting a magnetic resonance, wherein said method comprises:

a) application of a first magnetic field H1 to said spins A nuclei group, said field H1 oscillating in the quadrupolar resonance frequency of said spins A nuclei group, and simultaneously on said spins B nuclei group, other second and third magnetic fields, said second magnetic field being a magnetic field H0 which is turned on in coincidence with the first pulse of said oscillating magnetic field H1; and said third magnetic field being a magnetic field H2 oscillating within the magnetic resonance frequency of said spins B nuclei group in said magnetic field H0;

b) turning off said second magnetic field H0 when the signal of quadrupolar resonance from said spins A nuclei group is maximal, so that the signal-to-noise ratio of said quadrupolar signal increases, thereby decreasing the minimum volume of the compound able to be detected and/or analyzed;

c) digitalizing and summing detected signals while H0 is off, in synchronism with excitation pulses sequence for H1;

d) turning on again magnetic field H0 once the digitalization step ends;

e) repeating steps b) to d) until the adequate signal-to-noise ratio required to detect said compound is obtained; and f) emission of an alarm signal in the case of a positive detection or proceeding to the detection and/or analysis of the following compound should the signal be negative.

Yet another object is a method for the detection and/or analysis of compounds exhibiting double quadrupolar resonance.

Yet another object consists of sensor elements for the detection and/or analysis of compounds exhibiting nuclear quadrupolar resonance and nuclear magnetic resonance, or double nuclear quadrupolar resonance.

Yet another object is an arrangement which uses the sensor elements and circuits for the detection and/or analysis of compounds exhibiting nuclear quadrupolar resonance and nuclear magnetic resonance, or double nuclear quadrupolar resonance.

BRIEF DESCRIPTION OF THE DRAWINGS

The invention will be more clearly understood by means of the following figures.

a) an echo signal by pure quadrupolar resonance of the $^{35}Cl$ in paradichlorobenzene or p-$C_6H_4Cl_2$; and b) a signal of the echo of p-$C_6H_4Cl_2$ in double resonance, i.e. nuclear quadrupolar resonance (NQR) of the $^{35}Cl$ and magnetic resonance of protons ($^1H$).

Figure 1:
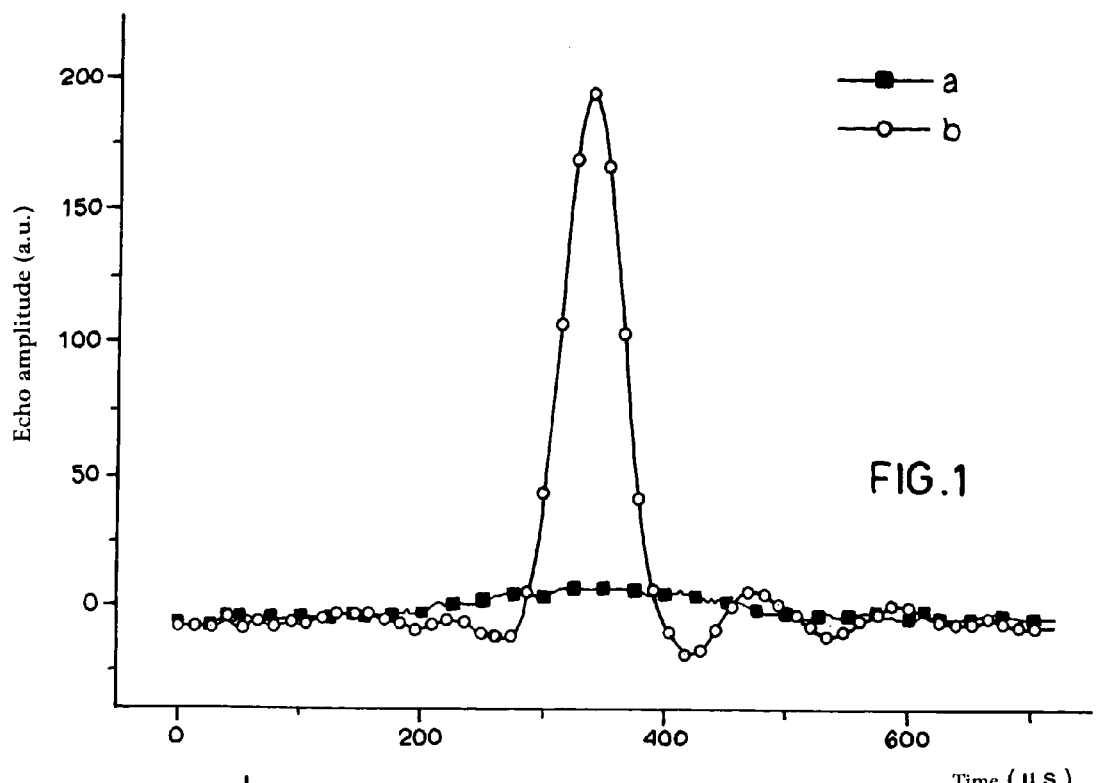
FIG. 1 shows.
Figure 2A:
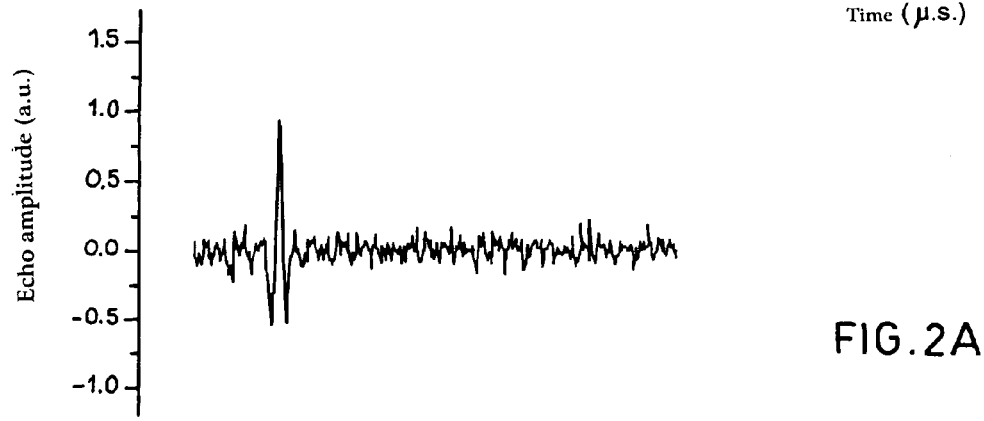

FIG. 2A illustrates spin echo of part b of FIG. 1, acquired in the presence of a 20 G time constant magnetic field.

Figure 2B:
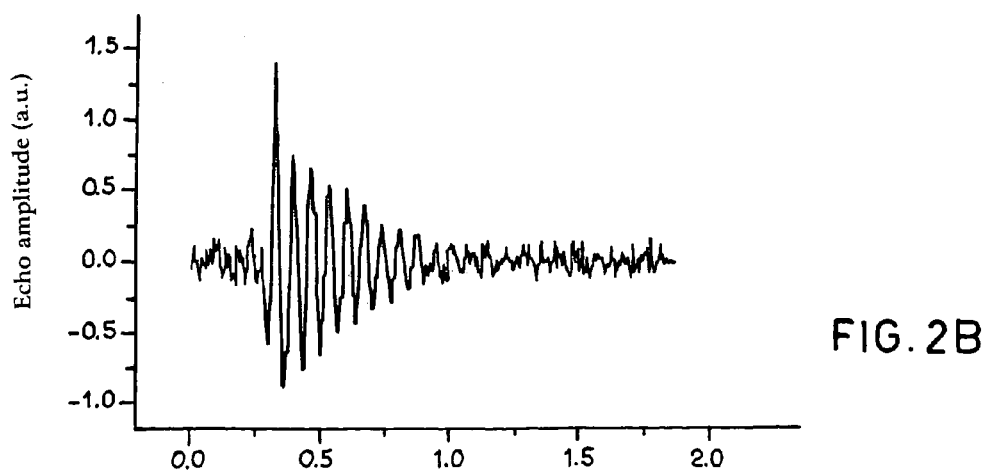

FIG. 2B illustrates echo of FIG. 2A, but cutting the 20 G time constant magnetic field at the maximum detection point, thereby increasing decay time and decreasing the minimum volume of compound to be detected and/or analyzed.

Figure 3:
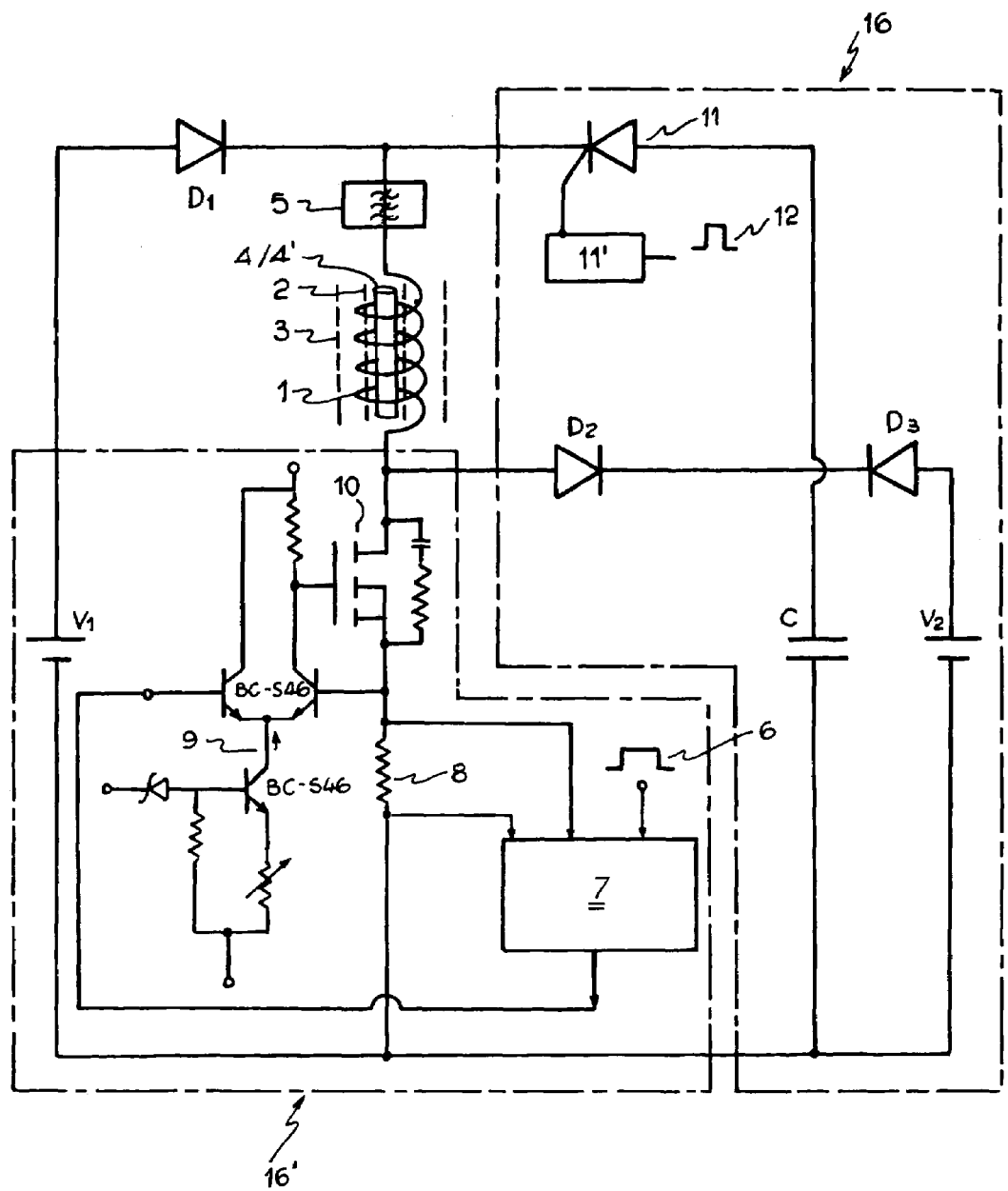

FIG. 3 illustrates a pulsed magnetic field $H_0$ generating circuit, connected to a solenoid coil.

Figure 4A:
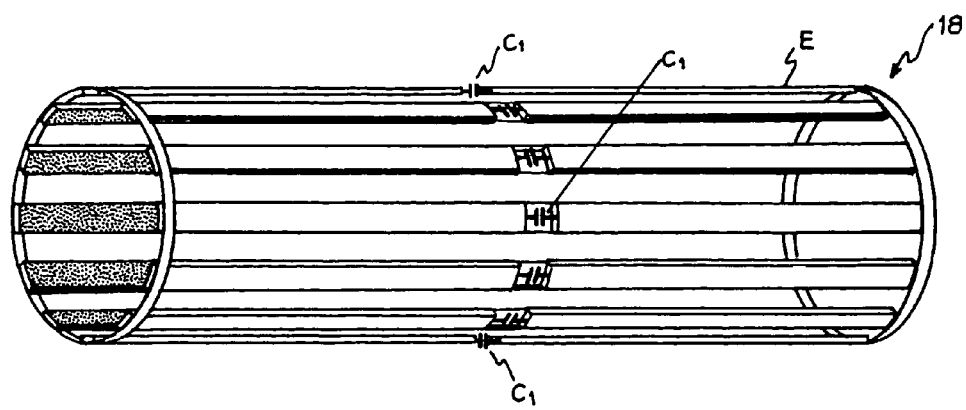
Figure 4B:
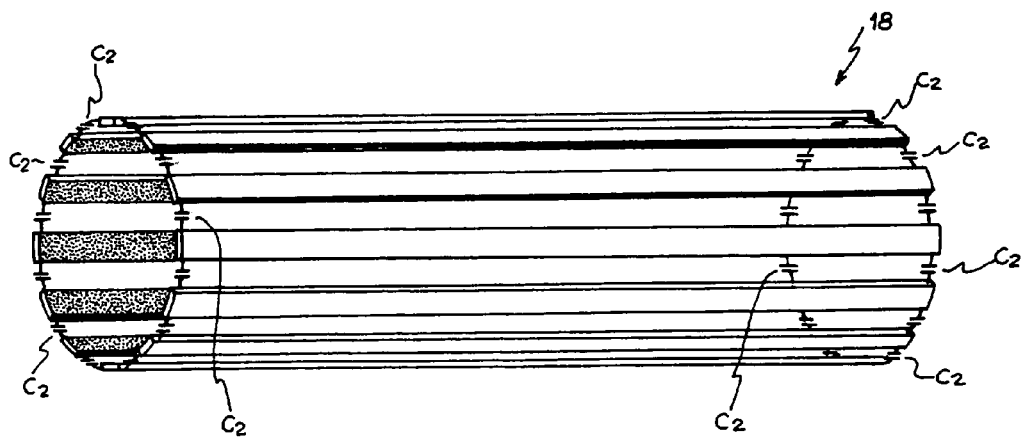

FIGS. 4A and 4B show different birdcage coils according to the prior art.

Figure 4C:
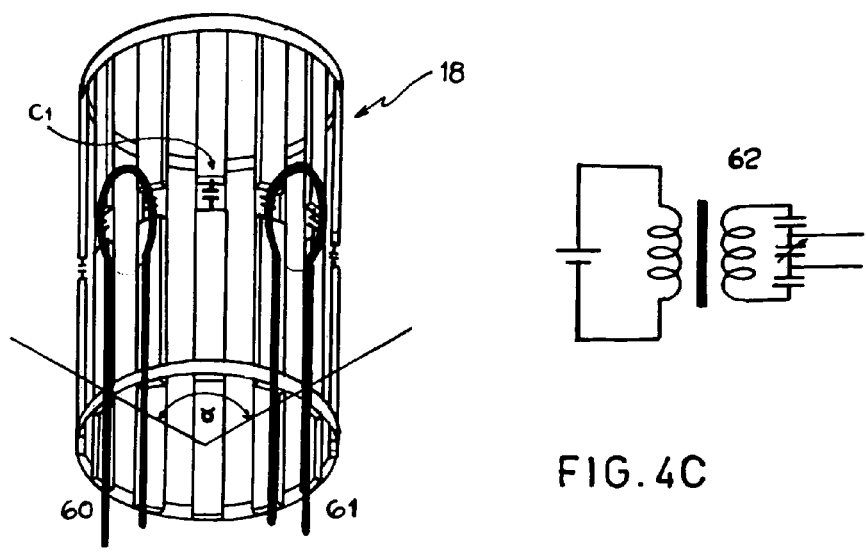

FIG. 4C shows a coupling circuit applied to the coil of FIG. 4A.

Figure 5A:
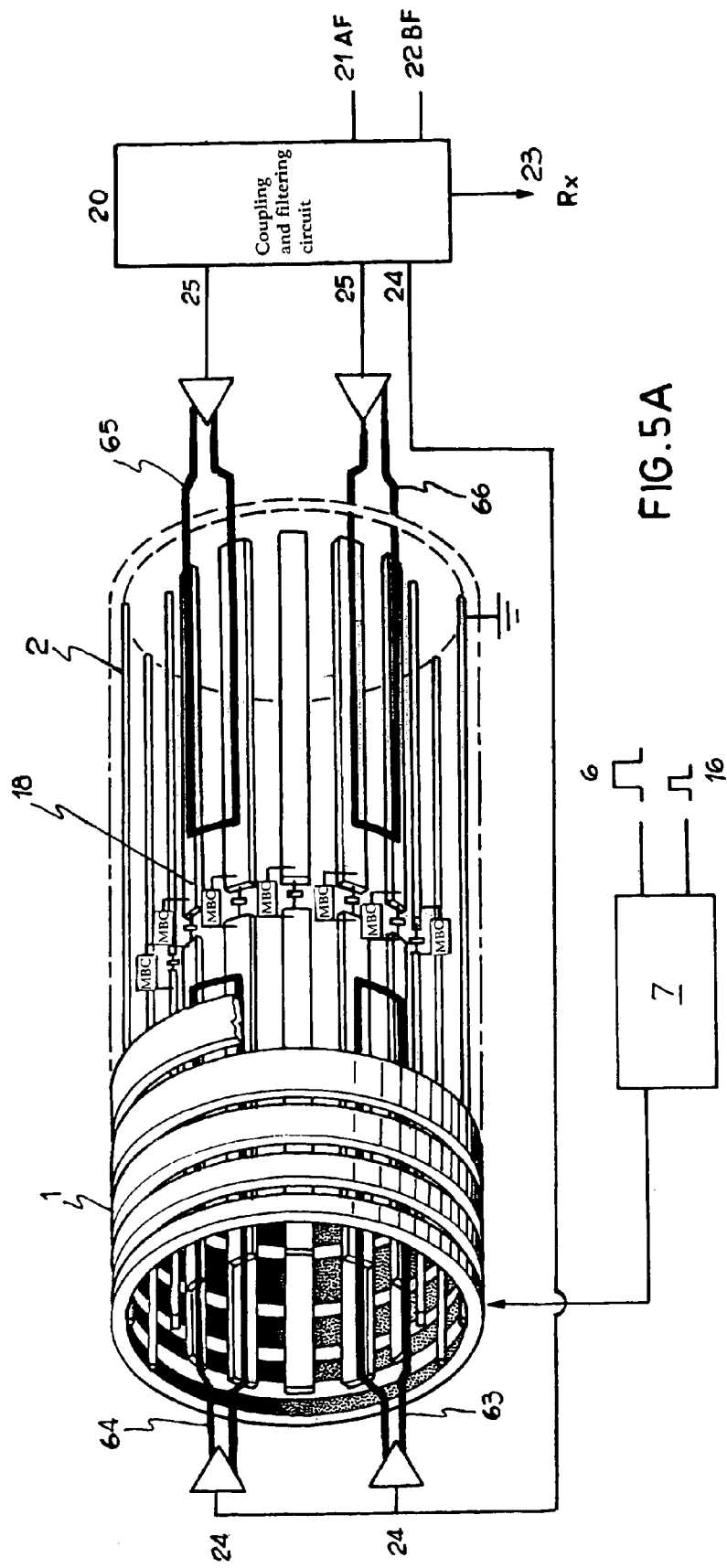

FIG. 5A shows a first embodiment of a sensor element according to the present invention.

Figure 5B:
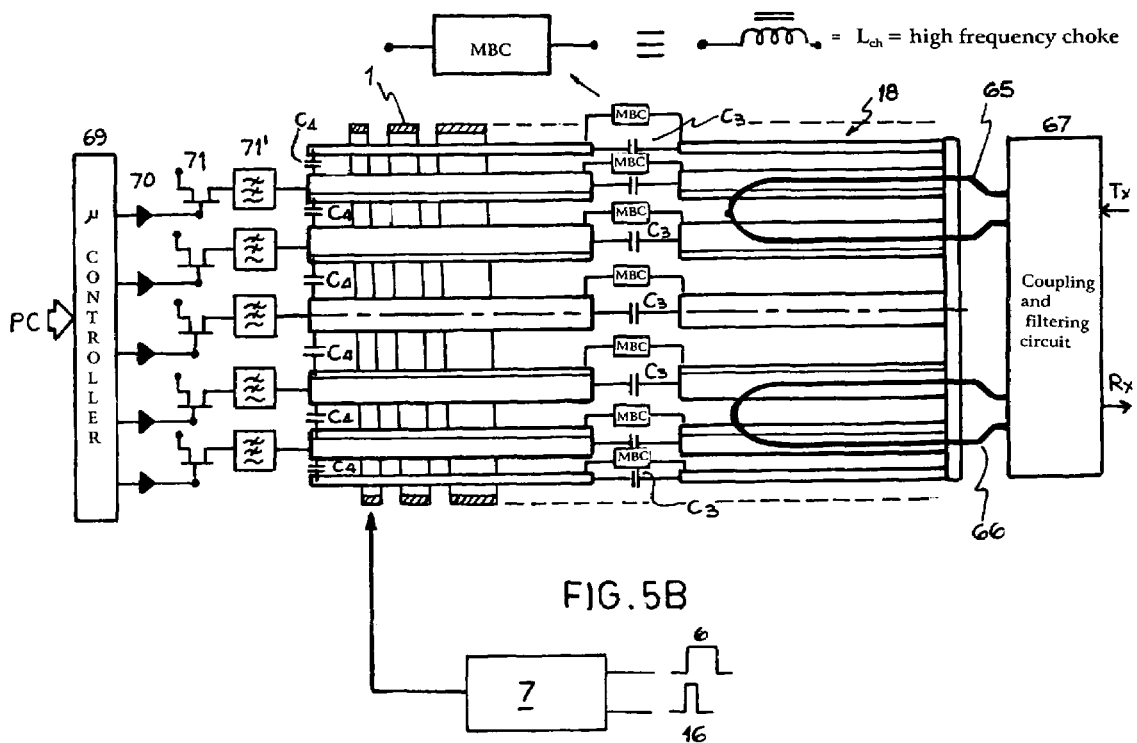

FIG. 5B shows a second embodiment of a sensor element according to the present invention.

Figure 5C:
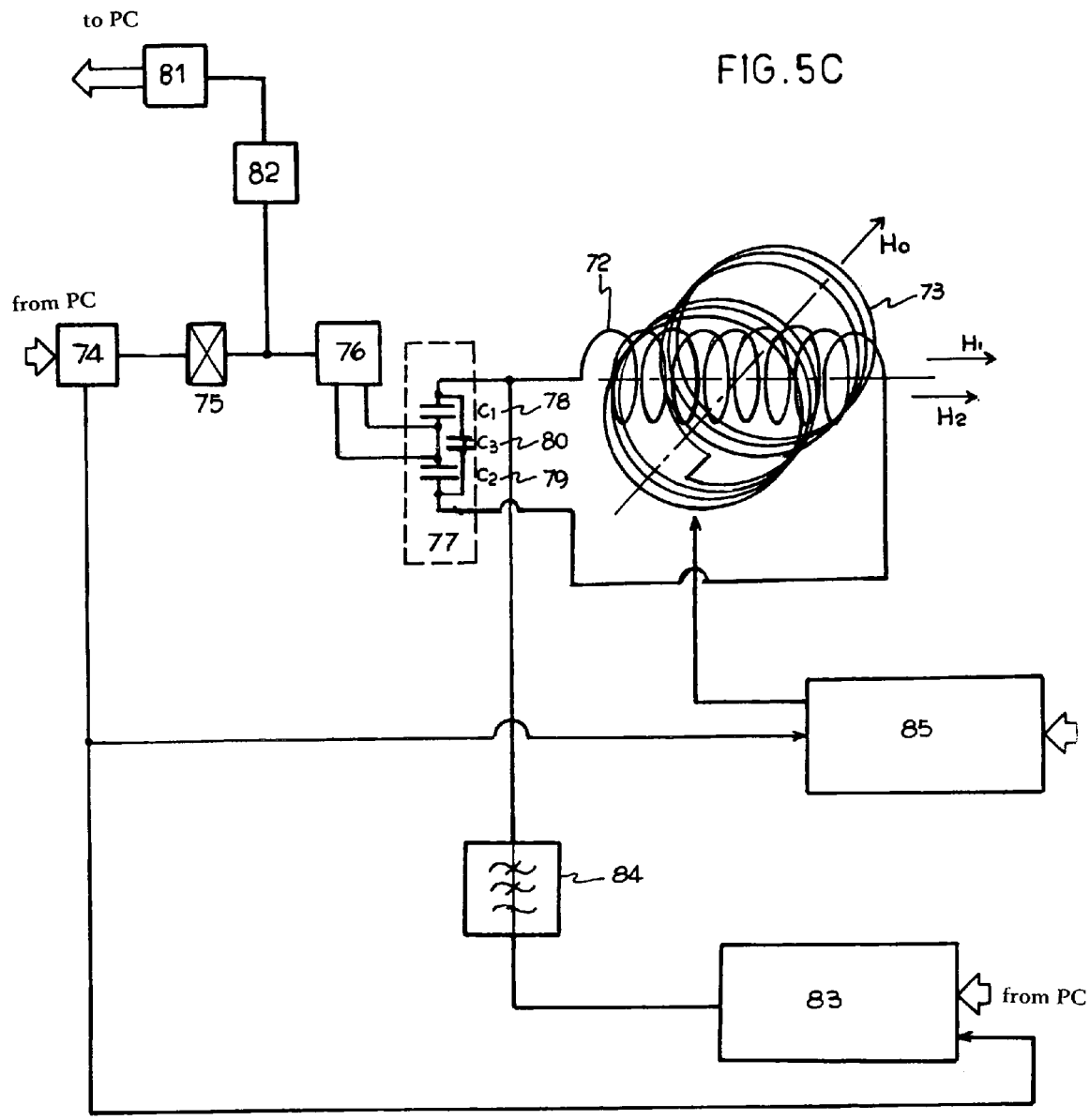

FIG. 5C shows a third embodiment of a sensor element according to the present invention.

Figure 6:
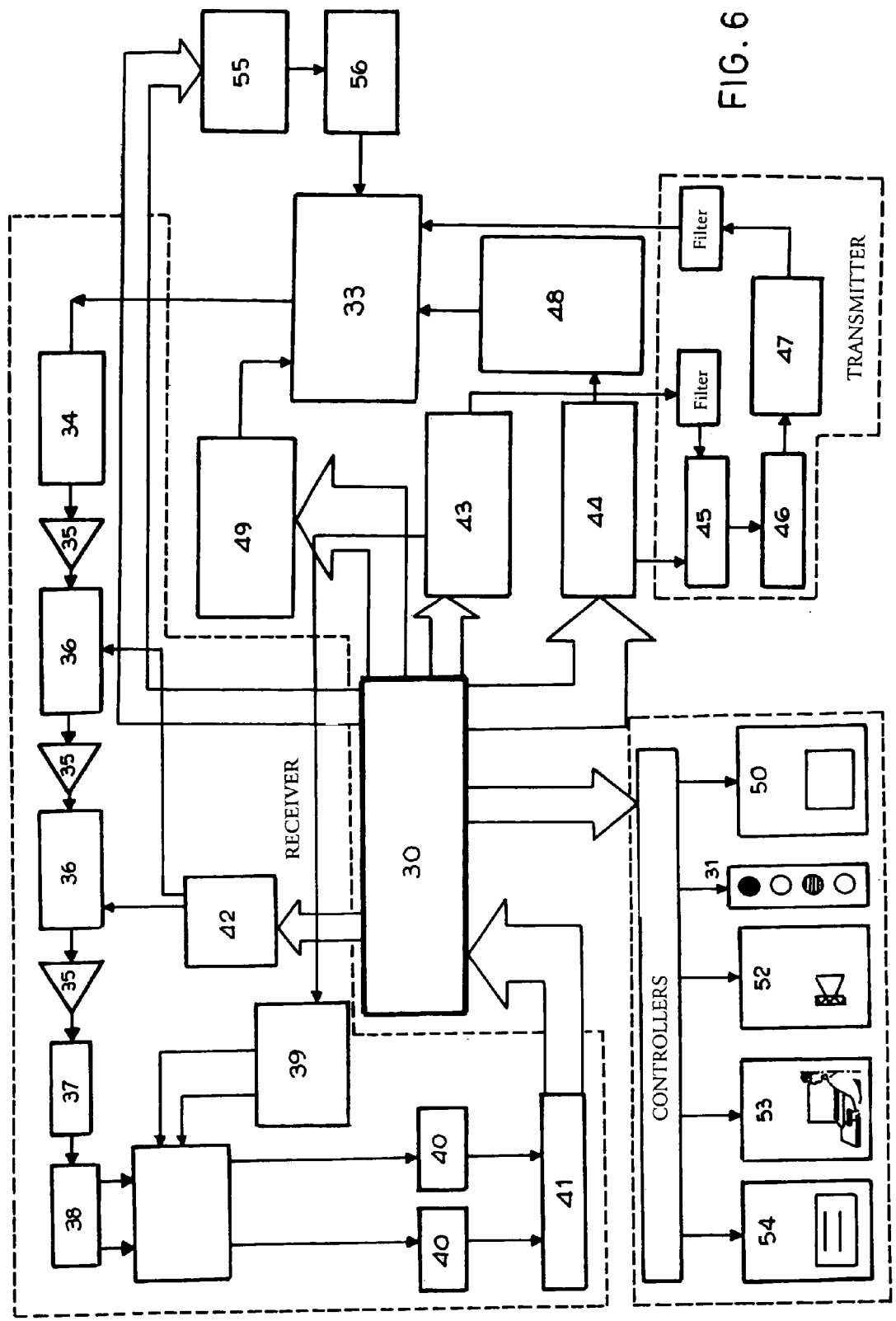

FIG. 6 illustrates a block diagram of the transmission/detection apparatus including a sensor element according to the invention.

Figure 7:
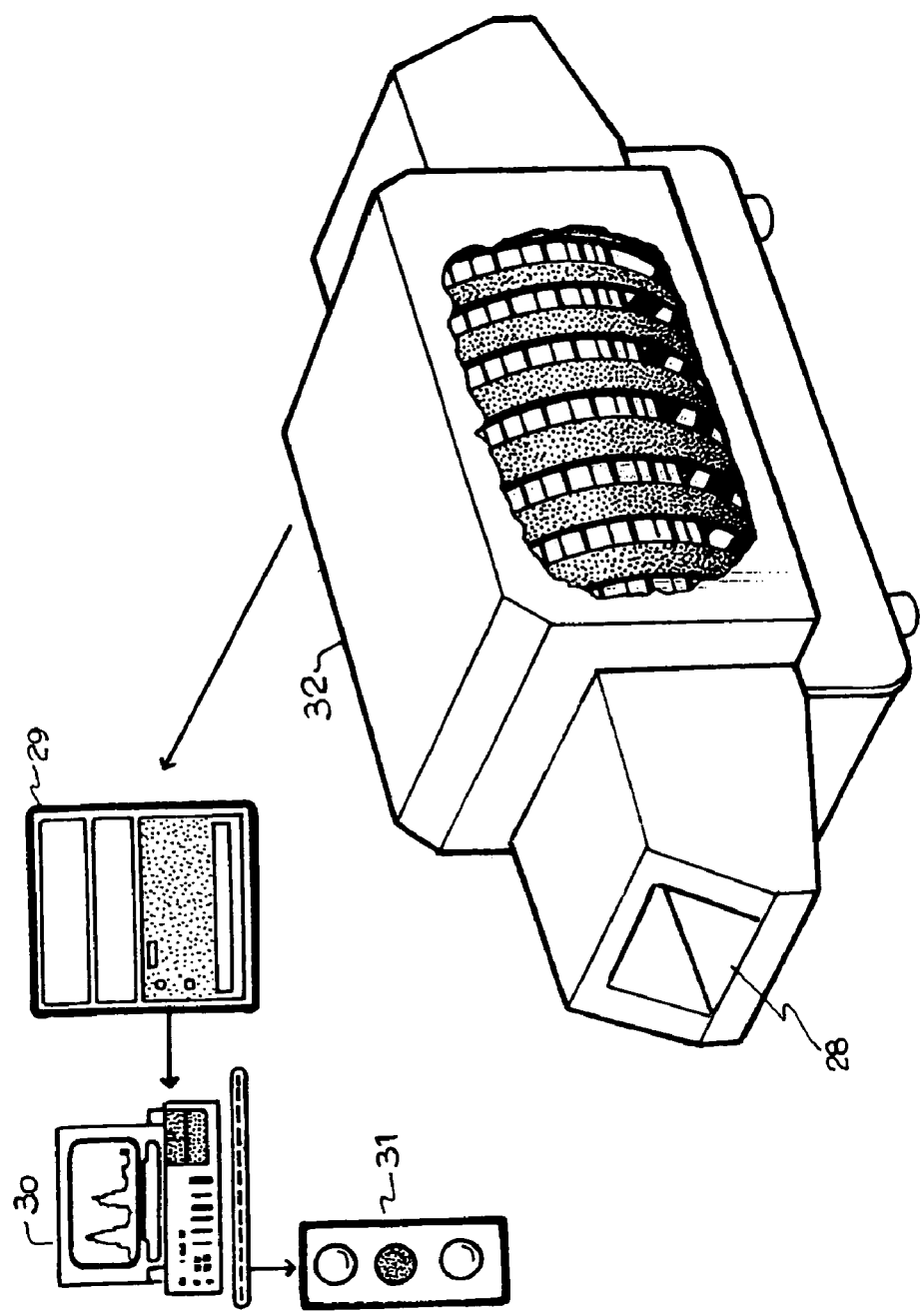

FIG. 7 illustrates an arrangement including a sensor element.

DETAILED DESCRIPTION OF THE PREFERRED EMBODIMENTS

Part a) of FIG. 1 illustrates the echo signal by quadrupolar resonance of a compound such as paradichlorobenzene or p-$C_6H_4Cl_2$, in the sequence $\pi/2$-$\pi$ for a pulse to pulse spacing $\tau=0.8$ ms, for a pure nuclear quadrupolar resonance situation of $^{35}Cl$.

Part b) of FIG. 1 illustrates an echo signal in double resonance condition, i.e. nuclear quadrupolar resonance (NQR) of $^{35}Cl$ upon the action of a high frequency magnetic field $H_1$, and nuclear magnetic resonance of protons $^1H$. Nuclear magnetic resonance condition of protons is achieved with a weak static field (known as Zeeman field) $H_0=21$ Gauss and an oscillating field $H_2=8$ Gauss with a frequency of oscillation of 90 KHz (J. Perlo, Final Paper for the Physics Degree, College of Mathematics, Astronomy and Physics, Universidad Nacional de Cordoba, Argentina (2000)).

FIG. 2A shows with more detail the spin-echo signal corresponding to the quadrupolar signal of part b) of FIG. 1, i.e. as from the DOR sequence, already exhibiting a strong gain respecting the signal that would be obtained by pure nuclear quadrupolar resonance (NQR).

FIG. 2B illustrates the same spin-echo signal as FIG. 2A but turning off magnetic field $H_0$ when such detected signal is at its maximum, i.e., applying the PUDOR sequence. When compared to FIG. 2A it can be seen that now echo increases in a relatively short time (the same as it takes to increase in FIG. 2A), and that when magnetic field $H_0$ is turned off just when the echo is maximum, the echo decreases very slowly, as in this case magnetization freely develops in the condition of pure nuclear quadrupolar resonance (NQR). The Fourier transform of the second half of the echo possesses a purer spectral content than in the case of DOR. That is to say, upon the turning off of field $H_0$ when the echo is at its maximum, the resonance line broadening effect during the detection period may be decreased. Accordingly the minimum volume of the compound to be detected/analyzed remarkably decreases, and at the same time the sensitivity of the detector increases.

Oscillating evolution of echo amplitude observed in FIG. 2B is due to the inclusion, upon the detection, of the process of resonant excitation and off resonant detection (TONROF). This process consists of the radiation of spins A nuclei groups with a field $H_1$, adjusted to its resonance frequence. To such end, the frequency of a direct digital sensor (SDD) is previously programmed, which sensor is associated to a spectrometer in resonance condition ("on resonance"). Then, at the beginning of the detection stage, frequence of said SDD synthetizer is changed by means of a command pulse originating from a pulse programmer. Then the signal is digitalized by means of an analog/digital converter, to an externally set frequency, e.g. on the order of 10 to 100 kHz out of the resonance condition ("off resonance"), whichever is more convenient.

Two simultaneous effects are achieved through the TONROF technique.

a) due to the fact that the signal-to-noise ratio increases with the digitalized signal frequency, and the detectability threshold for a lower quantity of compound is proportional to the lower signal amplitude which can be separated from noise, an increase of the signal-to-noise ratio directly implies a decrease regarding the volume of compound to be detected and/or analyzed; and b) when the digitalized signal frequency content is increased, the noise of the base and /or interference line of the quadrupolar signal produced by turning off of weak magnetic field $H_0$ may be easily filtered, e.g. by means of a digital filter.

This technique, as already stated, is applied in this invention both regarding double resonance DOR and double pulsed resonance, PUDOR, in combination with the previously described steady and non-steady sequences groups.

Cut time of $H_0$ is from 10 μs to 100 μs, preferably 10 μs, it is controlled by a MOSFET circuit as shown by FIG. 3, which we will describe below. In order to reduce said cut time of $H_0$ it may also be used a GTO electronic switches circuit such as that described in C. R. Rodriguez, "Estudio de la dinamica lenta y la estructura en cristales liquidos liotropicos miscelares mediante la RMN", Doctorate Thesis, College of Mathematics, Astronomy and Physics, Universidad Nacional de Cordoba, Argentina (2000).

That coil generating weak magnetic field $H_0$ may possess any of the generally used geometries: Maxwell's, solenoidal, ellipsoidal, saddle, superficial, etc. The design thereof provides for:

1) a uniform magnetic field $H_0$ at the volume occupied by compound to be detected and/or analyzed; and
2) the lowest possible inductance, in order to reduce on and off times of field $H_0$ to equally adequate values. In the case of the nuclear magnetic resonance (NMR) of spins B nuclei group, magnetic field required uniformity, $\Delta H_0/H_0$, is calculated from the bandwidth $\Delta\omega$ of spins B resonance and excitation bandwidth $\Delta\omega_2$ defined by $H_2(t)$. Spins B resonance bandwidth, $\Delta\omega$, is a characteristic of the compound to be detected, and for practical purposes and disregarding molecular dynamic effects, it may be expressed in magnetic field terms as $\Delta\omega=\gamma\Delta H$, wherein $\Delta H$ mainly refers to local fields sensed by protons in the molecule of the compound to be detected, $\gamma$ being the gyromagnetic coupling factor. In order to attain the double resonance maximum efficiency, it is required to excite in resonance all of the protons present at the volume occupied by the compound to be detected, thence it is reasonable to require the maximum variation of field $\Delta H_0$ to be in the order of the dispersion at local fields $\Delta H$ or lower, and that the bandwidth $\Delta\omega_2=\gamma\Delta H_2$ to comply with the maximum excitation condition, i.e. $\Delta\omega_2>\Delta\omega_0, \Delta\omega$.

Another requirement as regards weak magnetic field $H_0$ is its temporal stability. Said stability must be controlled so that the bandwidth of said $\Delta\omega_2=\gamma\Delta H_0(t)$ remains within the range imposed by $\Delta\omega_2$ during the full period of field application.

In order to fulfill such purpose there may be used Helmholtz coils, built by two assemblies of N turns spaced by a distance equal to the radius thereof, however, in general, depending of the bandwidth of the nuclear magnetic resonance (NMR) of the protons of the compound to be detected, the diameter of each assembly should be several times the diameter of the volume occupied by the compound to be detected and/or analyzed.

In order to reduce the coil volume generated by $H_0$, a solenoidal coil with variable width and pitch turns along the symmetry axis thereof has been developed, which axis is placed along the length of the inspection tunnel. Helix width to pitch ratio has been calculated according to the method proposed by E. Rommel, K. Mischker, G. Osswald, K. H. Schweikert and F. Noack, J. Magn. Reson. 70, 219 (1986).

For instance, a 70 cm long solenoidal coil, for a luggage inspection tunnel with 60 cm of free diameter, is built over at least one cylindrical form over which a copper helicoidal strip is deposited, the separation among turns being reduced to a distance shorter than 0.5 mm. There are other configurations possible, able to improve magnetic field cut time and/or spacial homogeneity at the volume useful for inspection, which are within the ability of the person technically skilled in the art.

This coil should also be shielded against the others comprising the sensor. This shield is done for the electro-magnetic uncoupling among coils to sufficiently attenuate electrical field, but not the magnetic field, at the volume occupied by the compound to be detected and/or analyzed. Shield possesses an adequate geometry capable of preventing generation of eddy currents which effect decreases quality factor Q of high and low frequency coil(s) which generate oscillatory magnetic fields $H_1$ and $H_2$ respectively. In order to achieve this effect adequate geometry cuts are made on the metallic film of shield, as for instance with the shape of bars, circles, etc.; or else, the $H_0$ generating coil may be built with a "self-shielded" geometry, e.g. among others bi-planar (see D. Tomasi, E. C. Caparelli, H. Panepucci and B. Foerster, "Fast optimization of a Biplanar Gradient Coil Set", Journal of Magnetic Resonance, 140, 325 (1999), E. C. Caparelli, D. Tomasi and H. Panepucci, "Shielded biplanar Gradient Coil Design", Journal of Magnetic Resonance Imaging, 9, 725 (1999)).

As a preferred but not limitative embodiment of the present invention, FIG. 3 illustrates a first solenoidal coil 1, with variable width and pitch turns along the symmetry axis thereof, interiorly surrounded by an inner shield 2 made from at least a preferably cylindrical epoxy layer with a copper film deposit, on which there have been constructed copper film sticks which are co-linear to said solenoidal coil 1 axis, and electrically grounded at one of their ends. As discussed below, in the case of those compounds which only exhibit nuclear quadrupolar resonance, solenoidal coil 1 and internal shield 2 will not be necessary.

An external shield 3, which construction is similar to that of internal shield 2, has the purpose of insulating sensor assembly from external electromagnetic pollution. Between internal shield 2 and tunnel free volume through which the luggage passes, there are positioned a second coil 4, which generates an oscillatory magnetic field of high frequency range $H_1$, and a third coil 4' which generates an oscillatory magnetic field of low frequency range $H_2$. This high and low frequency definition, applied to DOR and PUDOR, is merely intended to mean, for instance, that the first one is within the Megahertz range (nuclear quadrupolar resonance), and the second one within the range of the tens or hundreds of KHz (nuclear magnetic resonance in the presence of a weak magnetic field $H_0$. There could be a case in which both signals are within the Mhz range). A low-pass filter 5, connected to one of the ends of said first solenoidal coil 1, prevents the introduction of interferences between the high and low frequency coils 4 and 4' respectively. Electric power is delivered through a first power supply $V_1$, which is conveniently protected against countercurrents, preferably by means of a diode $D_1$. The other end of said solenoidal coil 1 is connected to a regulated circuit 16' consisting of a proportional controller which controls current circulating through a MOSFET's chain 10 (for example BUZ48) which operation in time is commanded by a first command pulse of field 6, from a pulse programming circuit 44 (see FIG. 7). Current intensity is controlled by a control device 7 from $H_0$. This control device 7 from $H_0$ senses current on a resistance 8 which is connected in parallel to said MOSFET's chain 10 and, through a proportional integrator-derivator (PID), commands a controller ("driver") comprised of transistors 9 (for example BC-546), to deliver the appropriate command current to said MOSFET's chain 10.

A starting circuit 16 consisting of a pair of diodes $D_2$ and $D_3$, a capacitor C, a second power supply $V_2$ and tiristor GTO 11, provides the extra power for the connection of current to solenoidal coil 1, in order to reduce connection time. Energy provided with power supply $V_2$ is stored in capacitor C. Diodes $D_2$ and $D_3$ perform protection functions for the countercurrents generated upon turning on and off that current generated by weak magnetic field $H_0$. A second command pulse 12, which we shall call "short pulse" 12, originating from pulse programming circuit 44 (see FIG. 7) commands said tiristor GTO 11 through another controller 11'. Short pulse 12 occurs immediately before the field command pulse 6, begins, connecting capacitor C to the solenoidal coil 1 circuit generating magnetic field $H_0$, and thus delivering to the solenoidal coil 1 all of the energy accumulated in said capacitor C. Voltage in $V_2$ is regulated until the desired $H_0$ intensity is achieved. It is convenient to remark that regulated circuit 16' may be replaced by a switch composed of a tiristor and its respective controller, which simply operates as a on/off switch, as stated in the above mentioned Doctorate Thesis of C. R. Rodriguez. This circuit is simpler and easier to implement, although it requires an excellent control on power supply $V_1$ in order to attain stability of field $H_0$, which is necessary for the experiments. Characteristic parameters of each particular application will dictate the implementation of either circuit.

FIGS. 4A and 4B illustrate two prior art models of birdcage coils 18. Coil 18 shown by FIG. 4A has its metallic turns E connected in series by means of capacitors $C_1$, this being a configuration known as "low-pass", and it generates oscillatory magnetic fields circularly polarized within the low frequency range. When the time-varying magnetic field bears circular polarization it can be also visualized as a rotary magnetic field with constant intensity or modulus.

Also, coil 18 on FIG. 4B has its metallic turns connected in parallel by means of capacitors $C_2$ and, as compared to FIG. 4A, this coil generates magnetic fields within the high frequency range. This configuration is known as "high-pass".

In both cases, couplings with excitation and detection circuits are inductively carried out, as known from the prior art and as illustrated by FIG. 4C, which shows the birdcage coil 18 of FIG. 4A coupled by mutual induction to two induction coils 60-61 which respond to a same excitation frequency, positioned in quadrature, and their coupling circuit 62 to transmitter-receiver is illustrated on the right.

Sensor elements described hereinafter comprise a number of coils capable of generating said three fields $H_0$, $H_1$ and $H_2$. More specifically, and with the purpose of reducing volume of said sensor element, a first embodiment of said sensor element will comprise a coil in order to generate said field $H_0$, and a birdcage coil, in order to simultaneously generate said fields $H_1$ and $H_2$. A second embodiment of said sensor element will comprise Helmholtz coils in order to generate said field $H_0$ and a solenoidal coil in order to simultaneously generate said fields $H_1$ and $H_2$.

On the other hand, spatial location of the different coils verifies what is known as a "filling factor", that is to say, that coil responsible for the generation of high frequency field $H_1$ affecting spins A nuclei group should be as close as possible to the volume of the compound to be detected and/or analyzed. This is already known in the art and we will not discuss it further. Accordingly, in the first embodiment of the sensor element, said birdcage coil 18 is surrounded by said solenoidal coil 1; and in the second embodiment, said solenoidal coil 1 is surrounded by the Helmholtz coils 73.

FIG. 5A illustrates a sensor element comprising a solenoidal coil 1 which surrounds a birdcage coil 18. Structure of said solenoidal coil 1 and corresponding associated circuits are preferably those mentioned when describing FIG. 3. Birdcage coil 18, on the other hand, simultaneously operates as a low-pass filter for low frequencies and as a high-pass filter for high frequencies. Said birdcage coil 18 is comprised of a series of turns E serially connected by means of capacitors $C_1$ and in parallel by means of capacitors $C_2$. In parallel with capacitors $C_1$ there are connected multiband coupling circuits, MBC, made up by circuits $L_3 C_3$ tuned with said capacitors $C_1$. When the frequency of the current passing through said turns E is on the order of the low frequency, capacitance of capacitors $C_2$ is such that they short-circuit at that frequency, and said coil 18 operates as that illustrated by FIG. 4A. On the contrary, should the frequency of current passing through turns E be on the order of the high frequency, capacitors $C_1$, aided by $C_3$ and $L_3$, are short-circuited and said coil 18 operates as in FIG. 4B. Said two high and low frequency currents circulate simultaneously through said coil 18. Any person technically skilled in the art will be able to determinate the values of $C_1$, $C_2$, $C_3$ and $L_3$ according to the required resonance characteristics, which are dictated by the type of compound to be detected and/or analyzed. High frequency coils 63-64 and low frequency coils 65-66 positioned in quadrature are coupled, by mutual induction, to said birdcage coil 18.

Said induction coils 63-66 tune said birdcage coil 18 to the respective resonance frequencies of spins A and B, and adapt their impedance regarding a coupling and filtering circuit 20. High-frequency excitation signals 21 and low-frequency signals 22 reach to said coupling and filtering circuit 20, from the respective generators. In turn, outlets of said coupling and filtering circuit 20 guide, on the one hand, the signal from receiver Rx 23, and on the other hand the high and low frequency excitation signals 24-25, outphased 90°, to high frequency and low frequency coils 63-64 and 65-66, respectively.

Outphased 90° excitation signals means that for each pair of high frequency or low frequency induction coils, the signal arriving to one of the pair coils is 90° outphased respecting the excitation signal arriving to the other. Also, the fact that coils are in quadrature means that for each pair of high-frequency or low-frequency coils, one of the coils is located 90° as regards the other as can be seen in FIG. 4C.

In those cases in which the excitation frequency of spins A is within the range of a few Megahertz, as with the quadrupolar resonance of nitrogen $^{14}N$, computation of capacitors with high-pass configuration results in values of difficult commercial obtention, whereby it is necessary to adopt the low-pass configuration at the birdcage coil, as shown by FIG. 4A. Birdcage coil, as described as follows, complies with such condition.

FIG. 5B shows a birdcage coil 18, also surrounded by a solenoidal coil 1 (not shown) as in FIG. 5A, adapted to contemplate the resonance low frequency condition of the spins A nuclei group previously discussed. In such a sense, capacitors $C_3$ connecting in series the different turns E, are calculated for said coil to tune by means of $H_1$, within the resonance frequency of the spins A nuclei group, which will be on the order of a few MHz. In parallel with each capacitor $C_3$ there are connected multiband coupling circuits, MBC, which for this case comprise a high frequency choke element $L_{ch}$ which operates like a high impedance for the spins A resonance frequency and as a short-circuit for the spins B resonance frequency. On the other hand, capacitors $C_4$ are inversely calculated, i.e. in such a manner that same operate like a short-circuit at the frequency of resonance of spins A and with a high impedance at the lower resonance frequency of spins B. Thus, in the case of signals induced at the resonance frequency of spins A, birdcage coil 18 operates under the low-pass configuration (FIG. 4A). In order to excite spins B nuclei group, a magnetic field $H_2$ is generated in a way which could be assimilated to the rotary field principle of an electric motor. A micro-controller 69 (or else, a signal digital processor or the like generates sequential current pulses which are transmitted to each of the turns E by means of an assembly of controllers 70, MOSFET's switches 71 and low-pass filters 71', controllers 70 being connected to the outlet of said micro-controller 69, low-pass filters 71' to each of the turns E of one end of said coil 18, and MOSFET's switches between said controllers 70 and said low-pass filters 71'. That is to say, we introduce an anti-resonant circuit which operates as a multiplexor which enables the birdcage coil 18 to operate at frequency for $H_2$ in the order of tens or hundreds of KHz. More specifically, the assembly formed by said micro-controller 69, controllers 70, MOSFET's chain 71 and low-pass filters 71', operates as a low frequency coupling and filtering circuit similar to the coupling and filtering circuit 20 of FIG. 5A, but in this case it is a direct and non-inductive coupling on said birdcage coil 18.

There is also contemplated another coupling and filtering circuit for high frequency 67 for the resonance frequency of the spins A nuclei group, which is connected to a transmitter Tx and a receiver Rx and a pair of coils 65-66, placed in quadrature and coupled by mutual induction to said birdcage coil 18. Said coils 65-66 are excited by high-frequency excitation signals which are outphased 90°.

Birdcage coil 18 advantage is that it generates circularly polarized fields, thus enabling, in the case of polycrystalline compounds, the collection of signals from crystals with multidirectional orientation regarding axis of coil 18, thus originating a better signal-to-noise ratio; and consequently, an increase on the detector sensitivity. On the contrary, quality factor Q remarkably decreases as regards that which may be obtained from solenoidal construction coils. When compared to solenoidal coils, this effect generates a worsening of the signal-to-noise ratio, (Y. K. Lee, H. Robert, D. K. Lathrop, "Circular Polarization Excitation and Detection in NQR", Journal of Magnetic Resonance, 148,355 (2001)). On the other hand a high value of Q. produces a spectrometer "dead time" which is significantly higher, and should same not be adequately controlled by a Q-damper type circuit, it can develop a signal-to-noise ratio of lower quality than that produced by a birdcage coil with lower "Q". That is, depending on the available electronic technology and the characteristics of the samples to be detected, it could be more desirable to replace the birdcage coil 18 with a solenoidal coil 72 as that described as follows.

FIG. 5C illustrates a solenoidal coil 72 with double oscillating field generation, $H_1$, and $H_2$. Said coil 72 is constructed with variable width and pitch turns with the object of obtaining homogeneous fields (see A. F. Privalov, S. V. Dvinskikh y H. M. Vieth, "Coil Design for Large-Volume High-BI Homogeneity for Solid-State NMR Applications", Journal of Magnetic Resonance, A 123, 157-160 (1996)). In this case, coil 72 axis coincides with the axis of the tunnel through which the compound to be detected and/or analyzed circulates. In a plane which is perpendicular to the longitudinal axis of said coil 72 there is placed the longitudinal axis of a pair of longitudinal Helmholtz 73 coils or their biplanar non-gradient variant, as per designs by E. C. Caparelli, D. Tomasi, y H.Panepucci, "Shielded biplanar Gradient Coil Design", Journal of Magnetic Resonance, 139, 725 (1999) or another with the same function. The exciter signal of the spins A nuclei group is generated at transmitter 74, passes through a pair of insulating cross diodes 75 and enters said solenoidal coil 72, after first passing through balanced-unbalanced transformer or "balum" 76. A coupling and filtering circuit 77 for the resonance frequency of spins A is tuned, in a configuration known as "balanced", to the solenoidal coil. Said coupling and filtering circuit 77 comprises a serial capacitors assembly 78 through 80; one of them being variable in order to attain said tuning in a balanced manner. It is not necessary to include another coupling and filtering circuit, as for this sensor element example, the field is linearly polarized.

Particularly, this embodiment of the sensor element is also applicable to those cases in which the frequency of resonance of the spins A nuclei group is low, i.e. a few Mhz, as in the case shown in FIG. 5B.

On the other hand, the generated nuclear quadrupolar resonance (NQR) signal enters the receiver/digitalizer assembly 81 by means of a quarter-wave-guide ($\lambda/4$) 82. The exciter signal of the spins B nuclei group originates from a pulsed generator, which is synchronized to a pulse generator (see FIG. 3), the frequency, phase and intensity of field $H_2$ being determined by a control computer 30 (see FIG. 7). A low-pass filter 84 insulates said pulsed generator 83 from solenoidal coil 72 high-frequencies. Lastly, a pulsed magnetic field generator 85 generates magnetic field $H_0$ at the Helmholtz 73 coils pair. In this scheme, $H_1$ and $H_2$ are again on a plane perpendicular to the direction of $H_0$.

The general rule is that magnetic fields $H_1$, $H_2$ should be as uniform as possible at the volume occupied by the detectable compound, and further, field $H_2$ direction should be necessarily arranged perpendicularly to $H_0$ direction, for the magnetic resonance condition of the spins B nuclei group to possess the maximum efficiency.

FIG. 6 shows a block diagram of the apparatus without mechanical parts, i.e. the assemblies, conveyor belt, etc. Exciter signal of quadrupolar nuclei of compounds generates from a transmitter and goes to sensor 33, which may be any of the above described.

Said sensor element detects the nuclear quadrupolar resonance (NQR) signal and guides same to the receiver. The signal enters said receiver through a receiver protecting device 34. This signal is amplified in several high-frequency amplifiers stages 35 and is filtered at filters 36 and 37. Then, the amplified signal enters the phase-sensitive detector 38 which along with divider and phase-shifter 39 form the spectrometer detector in quadrature. Lastly, the analog signal is converted into a digital one at converter A/D 41, after being filtered once again by filters 40. Digital signal is introduced into the control computer 30 for the analysis thereof and further decision making. Receiver amplifiers gain is controlled by the computer via controllers 42, in order to be able to adequate same to the volume of each particular compound. Returning to the issue of how an excitation signal is generated, we begin from the high frequency pulse which is generated at the direct digital synthesizer (DDS) 43, which is commanded by computer 30, and digital pulses originated from pulse programmer 44, also commanded by computer 30. Both pulses enter the high frequency switch 45, which signal is amplified at pre-amplifier 46 and power amplifier 47, and thus there are generated high frequency power pulses which are in charge of exciting quadrupolar nuclei (nuclei group of spins A, typically $^{14}N$ and $^{35}Cl$) pertaining the compound to be detected and/or analyzed by sensor 33, due to the action of magnetic field $H_1$. Pulse programmer 44 also commands circuit of quality factor change Q48. In this manner dead time of spectrometer 29 is substantially reduced (see FIG. 7), increasing the signal-to-noise ratio and thence decreasing the minimum volume of the compound to be detected and/or analyzed. This dead time is defined as that occurring immediately after the high frequency pulse is turned off. In this time energy remains stored at the (birdcage 18 or solenoidal 72) coil, which overlaps the very weak nuclear quadrupolar resonance (NQR) signal shielding detection. The change of quality factor Q48 allows a quick decrease of energy stored at the (birdcage 18 or solenoidal 72) coil, thus enabling the signal detection when the finalization of the high frequency pulse is nearest. As the nuclear quadrupolar resonance (NQR) signal of some compounds depends on the temperature, it is necessary to maintain a self-tuning process of spectrometer 29 (illustrated by FIG. 7) in order to analyze different resonance frequencies, according to the temperature of the compound in the interior of the luggage to be inspected. To such end it has been introduced the self-tuning circuit 49. Finally, the control computer 30 commands different alarm and information outlets. Silent alarm 50, audio output 52, visual output at a display 53, and graphic output 54. A lights assembly 31 (see also FIG. 7) instructs passenger and operator on the different actions to be taken: for example, a green light means that passenger/luggage must proceed, the inspection having been successfully passed, yellow light means that the inspection must be repeated, red light is a visual alarm for security personnel and white light means out of service. The quality factor Q48 change circuit comprises PIN type diodes connected in opposition and commanded by a control pulse from the pulse programmer 44. The purpose of the assembly of cross diodes and opposing Zener is to decrease the low-frequency noise, usually produced by diodes PIN. In order to protect receiver against the high-frequency pulses from the transmitter high-frequency pulses, usually a quarter-wave line (not shown) is included with the sole purpose of preventing manipulation of a coaxial cable which produces the same effect but that at a frequency of a few MHz its length makes its handling difficult. Lastly, the self-tuning device 49 consists on adding or subtracting capacitance to the syntony capacitor(s) (according to the type of coil to be used) via one or more coaxial type relays. Lastly, the low-frequency excitation signal generated by magnetic field $H_2$ is generated at the generator or respective micro-controller 55, which is commanded by computer 30, through the low frequency amplifier 56, before entering sensor 33. This block diagram of the apparatus is applicable to compounds exhibiting quadrupolar double resonance. It should be supplemented with the block diagram of the apparatus for the $H_0$ generation, described by FIG. 3, in those cases in which the compound to be detected and/or analyzed simultaneously possesses nuclear quadrupolar resonance and nuclear magnetic resonance.

As an application example, FIG. 7 shows a schematic view of an arrangement using a sensor element. External housing 32 may have the same aspect of the inspection apparatuses typically used at airports and operating by radiation of luggage with X-rays. This housing 32 bears in its interior the sensor element. Luggage 27 is introduced into the tunnel of cross dimensions X and Y, via conveying belt 28. External dimensions, represented by A, B, and C, depend on the sensor volume, which in turn depends on the size of the luggage to be inspected. Such dimensions are on the order of the typical dimensions of current airports inspection devices. Excitation signals for magnetic fields, as well as the detected nuclear quadrupolar resonance (NQR) signal are generated the former at the transmitter and the latter at the detector-receiver, both devices located at spectrometer 29. Computer 30 controls all the detection process in a manner such as to render it fully automatic, collecting at the same time the already digitalized nuclear quadrupolar resonance (NQR) signal and commanding, among other indicators, visual alarms 31.

Should it prove necessary, the low-frequency magnetic field $H_2$ may be pressed in synchronicity with $H_0$ pulses, as it is only effective when $H_0 \neq 0$. This possibility is mentioned for those cases in which it is not possible to conveniently insulate nuclear quadrupolar resonance (NQR) signal produced by spins A against interferences produced by $H_2$.

Lastly, we will discuss the quadrupolar double resonance of those compounds in which the quadrupolar nucleus is mainly coupled to another quadrupolar nucleus of another resonance frequency, as for example: nitrogen with potassium, sodium, etc. The spins A nuclei group is still directly observable by quadrupolar resonance, e.g. nitrogen or chlorine, and the spins B nuclei group is formed by any of its nuclei, for example, a small constant of quadrupolar coupling, and thence not directly detectable, but strongly coupled to nitrogen. In this particular case, it is not necessary to include static $H_0$ magnetic field. There will only be necessary two magnetic fields, $H_1$ and $H_2$, the first oscillating at the frequency of the quadrupolar resonance corresponding to the spins A nuclei group and the second at the frequency of the quadrupolar resonance corresponding to the spins B nuclei group, according to the quadrupolar spectrum of said spins B nuclei group. In other words, there will not be necessary neither solenoidal coil 1 of FIGS. 5A and 5B nor Helmholtz coils of FIG. 5C, both generators of weak magnetic field $H_0$, as only with a birdcage coil 18 as that shown by FIGS. 5A or 5B, or a solenoidal coil 72 as that shown by FIG. 5C there could be generated said two magnetic fields $H_1$ and $H_2$. Should both quadrupolar resonance frequencies be high, that is to say, in the MHz range, sensor elements of FIGS. 5A and 5C will be those of preferred application, otherwise there will be preferred sensor elements corresponding to FIGS. 5B and/or 5C. As previously mentioned, the higher of the two frequencies is defined as high frequency, and the lower of the two frequencies is defined as low frequency. Multiband couplings circuits (MBC) and coupling and filtering circuits may be calculated by any person technically skilled in the art, in order that they comply with the above functions. Allocation of spins A and B is carried out in order to define as spins A nuclei group those bearing the best pure nuclear quadrupolar resonance (NQR) signal.

Quadrupolar resonance frequency of the spins B nuclei group possesses a quadrupolar coupling constant, which is generally small, and that will depend in the quadrupolar spectrum of said spins B nuclei group. Magnetic field $H_1$, to which spins A nuclei group is subjected, is uniform and oscillates in high frequency, and magnetic field $H_2$ to which said spins B nuclei group is subjected, is uniform and oscillates in high or low frequency, according to the quadrupolar spectrum of nuclei B.

Detected quadrupolar resonance signal may be obtained by means of a spin-echo signals sequence.

Same may also be obtained via the procedure of resonant excitation and off resonant detection (TONROF) which will consist of:
   radiating spins A nuclei group with said first magnetic field $H_1$ adjusted to its resonance frequency;
   programming frequency of a direct digital synthetizer (DDS) associated to a spectrometer on resonance;
   during the detection stage, changing frequency of said synthetizer (DDS) by means of a command pulse from a pulse programmer in order to increase the signal-to-noise ratio; and
   digitalizing the signal by means of an analog/digital converter at a fixed frequency on the order of 10-100 kHz, as appropriate.

Also, said TONROF technique may be combined with sequences of single or compound pulses, known as steady and non-steady, as described as follows.

Said TONROF procedure may be applied to a steady sequence of single pulses known as steady state free precession (SSFP) consisting of:
   radiation of the sample with successive pulses of $\pi/2$ on the spins A nuclei groups; and
   digitalization of the quadrupolar signal thereof at the intervals between pulses.

The TONROF technique may be also applied to a steady sequence of single pulses known as strong off resonant (SORC), wherein both quadrupolar signals are excited and detected in the off-resonant status.

Lastly, it may also be applied to a non-steady sequence known as spin lock spin echo (SLSE), which maintains the nuclear quadrupolar resonance (NQR) echo signal during an effective time $T_2$ higher than the $T_2$ decay of the pulses sequence, and consisting of:
   the application to the compound of a first high frequency from said first magnetic field $H_1$ with an amplitude such as to reorientate magnetization of quadrupolar nuclei at a 90° angle and with a 0° phase for said direct digital synthetizer (DDS);
   after a period of time $\tau$, the application of a new high-frequency pulse, now of double duration or able to reorientate sample 180° and with the phase at 90° regarding that of the previous pulse in order that, exactly at the same period $\tau$ from the ending of said new high frequency pulse, the spin echo appears;
   repeating the previous step until n echoes are collected, and then digitalizing and summing same.

As regards sensor elements used for the detection and/or analysis of compounds which simultaneously exhibit double nuclear quadrupolar resonance, it must be borne in mind that the generation of a weak magnetic field $H_0$ will not be necessary.

A preferred sensor element comprises a first coil 4 which generates a first high-frequency oscillating magnetic field $H_1$ and a second coil which generates a second high or low frequency oscillating magnetic field $H_2$ 4', according to the quadrupolar spectrum of nuclei B. An internal shield 2 is arranged between said coils 4,4' and the free volume of the tunnel the compound to be detected/analyzed is to travel through. In turn, said coils 4,4' are surrounded by an external shield 3, as shown by FIG. 3, not including solenoidal coil 1 or the circuit associated for the generation and control of field $H_0$.

Said first coil 4 and second coil 4' may conform, as in previous examples, a single birdcage coil 18 as shown by FIGS. 5A or 5B, provided the first magnetic field $H_1$ oscillates at high frequency, the second magnetic field $H_2$ being able to oscillate at high or low frequency, according to the quadrupolar spectrum of nuclei B. Particularly, a birdcage coil 18 as that illustrated by FIG. 5A will comprise a plurality of turns E connected in series by means of capacitors $C_1$, and in parallel by means of capacitors $C_2$, multiband coupling circuits (MBC) connected in parallel to said capacitors $C_1$, and induction coils 63-64 and 65-66 for the high- and low-frequencies, respectively, which are placed in quadrature, and excited with signals out-phased at 90°. Said coils are connected to a coupling and filtering circuit 20 as that shown by FIG. 5A.

Multiband coupling circuit (MBC) is formed by a circuit $L_3C_3$ which is tuned to said capacitor $C_1$ and the high and low frequencies bands simultaneously circulate through said turns E in such a way that, should the current passing through said turns E be in the high frequencies band, capacitor $C_1$ short-circuits with the aid of the MBC and said birdcage 18 operates as a high-pass filter, and should the current passing through said turns E be in the low frequencies band, capacitor $C_2$ short-circuits and said birdcage will operate as a low-pass filter. Internal shield 2 is constructed from at least a preferably cylindrical sheet made of epoxy material with a copper film deposit with adequate geometry cuts, as for example bars, circles, etc., over which there are constructed copper film sticks parallel to the longitudinal axis of the luggage inspection tunnel, one of the ends thereof being electrically grounded.

Another embodiment of a birdcage coil 18 is similar to that shown by FIG. 5B, which contemplates the condition of low frequency of resonance of spins A nuclei group. In such sense, capacitors $C_3$ which connect in series different turns E, are calculated so that said coil tunes by means of $H_1$ at the frequency of resonance of the spins A nuclei group, which will be in the range of a few MHz. In parallel with each capacitor $C_3$ there are connected multiband coupling circuits which comprise an element by high frequency choke $L_{ch}$ which behaves as a high impedance for the resonance frequency of spins A, and as a short-circuit for the lower resonance frequency of spins B. On the other hand, capacitors $C_4$ are inversely calculated, that is, in such a way that they operate as a short-circuit at the resonance frequency of spins A, and with a high impedance at the lower frequency resonance of spins B. Thus, for signals induced at the resonance frequency of spins A, birdcage coil 18 operates as a low-pass filter (FIG. 4A), a magnetic field $H_1$ being created which is assimilable to the rotating field principle of an electrical motor. A microcontroller 69 (or a signals digital processor or similar device) generates current sequential pulses which are transmitted to each of the turns E by means of a set of controllers 70, MOSFET's switches 71 and low-pass filters 71', controllers 70 being connected to the outlet of said micro-controller 69, low-pass filters 71' to each of the turns E of said birdcage 18, and the MOSFET's switches between said controllers 70 and said low-pass filters 71'. That is to say, we introduce an anti-resonant circuit which operates as multiplexor, thereby allowing birdcage coil 18 to operate at a frequency, for $H_2$, in the range of tens to hundreds of KHz. More specifically, the assembly comprised by said micro-controller 69, controllers 70, MOSFET's chain 71 and low-pass filters 71' operates as a coupling and filtering circuit similar to the coupling and filtering circuit 20 of the previous example, but in this case it is a direct and non-inductive coupling on said birdcage coil 18.

Another coupling and filtering circuit 67 is further provided for the spins A nuclei group resonance frequency, which is connected to a transmitter Tx and a receiver Rx. Said coupling and filtering circuit 67 excites induction coils 65-66 placed in quadrature and mutually induction coupled to said birdcage coil 18 by means of signals out-phased at 90°.

Lastly, a sensor element similar to that shown by FIG. 5C may be used which will only include a solenoidal coil 72 which simultaneously generates a first magnetic field $H_1$ and a second magnetic field $H_2$. Said coil 72 comprises turns of variable width and pitch; a transmitter 74 which generates an excitation signal; a pair of cross diodes 75 connected at the outlet of said transmitter; a "balum" transformer 76 connected to the outlet of said pair of cross diodes 75; a coupling and filtering circuit 77 for the adequately tuned high frequency, connected at the outlet of said transformer 76, and constituted of a plurality of capacitors 78 to 80, one of them being variable in order to allow the tuning of the coupling and filtering circuit 77 to solenoidal coil 72. The inclusion of a further coupling and filtering circuit is not required, because for this example of sensor element the field is linearly polarized. There is also included a receiver/digitalizer assembly 81 into which the signal enters via a quarter-wave-guide ($\lambda/4$) connected between said cross diodes pair 75 and said balanced-unbalanced transformer 76. Digitalized signal is processed by the control computer 30.

Block diagram of the apparatus, associated to the above several sensor elements, does not contemplate control and regulating circuits of pulsed field $H_0$ of FIG. 2. Sensor element will be a birdcage coil 18 which does not include solenoidal coil 1 shown by FIGS. 5A and 5B, or a solenoidal coil 72 which does not include Helmholtz coils shown by FIG. 5C.

Arrangement which includes the above sensor elements, in order to detect and/or analyze compounds which simultaneously exhibit double nuclear quadrupolar resonance, is similar to that shown by FIG. 7.

What is claimed is:

1. A method for at least one of detection or analysis of a test compound or object that may contain a compound bearing spin A nuclei having a quadrupolar resonance frequency and capable of exhibiting a quadrupolar resonance; and spin B nuclei having a magnetic resonance frequency and capable of exhibiting a magnetic resonance, said method comprising:
   a) radiating the test compound or object with a first magnetic field $H_1$ oscillating in the quadrupolar resonance frequency of the spin A nuclei in an excitation pulse sequence comprising a first high frequency pulse of $\pi/2$ and; a second weak magnetic field $H_0$ in a second pulse sequence that is turned on at the same time as the first high frequency pulse of said magnetic field $H_1$; and a third magnetic field $H_2$ oscillating within the magnetic resonance frequency of said spin B nuclei in said magnetic field $H_0$;
   b) turning said second magnetic field $H_0$ off when a signal of quadrupolar resonance from said spin A nuclei is maximal and then detecting signals with a receiver;
   c) digitizing and summing detected signals while said second magnetic field $H_0$ is off;
   d) turning said second magnetic field $H_0$ on again once the digitizing step ends; and
   e) repeating steps b) to d) to increase the signal-to-noise ratio and then analyzing the digitized and summed signals for the nuclear quadrupolar resonance of the compound.

2. The method according to claim 1, wherein if an adequate signal to noise ratio for the detection or analysis of the compound is not obtained, said method further comprises waiting for said spin A nuclei to relax and reach thermal balance and then repeating steps a)-e).

3. The method according to claim 1, wherein the time between turning said second magnetic field $H_0$ off in step b and turning said second magnetic field $H_0$ on in step d is 10 to 100 μs.

4. The method according to claim 1, wherein said signal of quadrupolar resonance is obtained by means of a spin-echo sequence.

5. The method according to claim 1,
   wherein step b comprises issuing a command pulse from a pulse programmer when said second magnetic field $H_0$ is turned off to change the frequency of a direct digital synthetizer (DDS) to the frequency of $H_1$ plus an offset frequency; and wherein in step c, the digitizing and summing of said signal of quadrupolar resonance is accomplished by an analog/digital converter at a fixed frequency on the order of 10 to 100 kHz off resonance, and by filtering at least one of a base or signal interference line noise persisting after said second magnetic field $H_0$ is turned off.

6. The method according to claim 1, wherein said third magnetic field $H_2$ is pulsed in synchrony with pulses of the second pulse sequence.

7. The method of claim 1 further comprising emitting an alarm signal if the compound is detected.

* * * * *